(12) United States Patent
Chaudhari et al.

(10) Patent No.: US 9,085,521 B2
(45) Date of Patent: Jul. 21, 2015

(54) CATALYST SYSTEM AND PROCESS FOR CONVERTING GLYCEROL TO LACTIC ACID

(75) Inventors: Raghunath V. Chaudhari, Lawrence, KS (US); Bala Subramaniam, Lawrence, KS (US); Debdut S. Roy, Manjusar (IN)

(73) Assignee: UNIVERSITY OF KANSAS, Lawrence, KS (US)

( * ) Notice: Subject to any disclaimer, the term of this patent is extended or adjusted under 35 U.S.C. 154(b) by 177 days.

(21) Appl. No.: 13/432,947

(22) Filed: Mar. 28, 2012

(65) Prior Publication Data

US 2012/0253067 A1 Oct. 4, 2012

Related U.S. Application Data

(60) Provisional application No. 61/469,417, filed on Mar. 30, 2011.

(51) Int. Cl.
| | |
|---|---|
| *C07C 51/295* | (2006.01) |
| *C07C 51/16* | (2006.01) |
| *C07C 59/08* | (2006.01) |

(52) U.S. Cl.
CPC ...................... *C07C 51/16* (2013.01)

(58) Field of Classification Search
CPC .......... C07C 51/16; C07C 51/23; C07C 59/08
See application file for complete search history.

(56) References Cited

U.S. PATENT DOCUMENTS

| | | |
|---|---|---|
| 7,829,740 B2 | 11/2010 | Enomoto et al. |
| 7,923,514 B2 | 4/2011 | Takahashi et al. |
| 2013/0225787 A1* | 8/2013 | Baets et al. ........... 528/361 |

FOREIGN PATENT DOCUMENTS

| | | |
|---|---|---|
| CN | 101695657 | 4/2010 |
| NL | EP 0201957 A2 * | 4/1986 |

OTHER PUBLICATIONS

White et al, Basic Energy Sciences Advisory Committee Subpanel Workshop Report, Opportunities for Catalysis in the 21st Century, 2002, pp. 1-47.*
Anonymous, RD 468024, Dehydration of Glycerol, 2003, pp. 1-2.*
Marincerean et al, Catalysis of Organic Reactions, 2007, pp. 427-436.*
Maris et al, Journal of Catalysis, Hydrogenolysis of Glycerol Over Carbon-supported Ru and Pt Catalysts, 2007, 249, pp. 328-337.*
Kishida et al., *Conversion of Glycerin into Lactic Acid by Alkaline Hydrothermal Reaction*, Chem. Lett. 34(11) 1560-1561 (2005).
Marincean et al., *Glycerol hydrogenolysis to propylene glycol under heterogeneous conditions*, Chemical Industries 115 (Catalysis of Organic Reactions), 427-436 (2007).
Maris et al., *Glycerol hydrogenolysis on carbon-supported PtRu and AuRu bimetallic catalysts*, J. Catal. 251 281-294 (2007).
Shen et al., *Effect of Alkaline Catalysts on Hydrothermal Conversion of Glycerin into Lactic Acid*, Ind. Eng. Chem. Res. 48 8920-8925 (2009).
Shen et al., *Efficient synthesis of lactic acid by aerobic oxidation of glycerol on Au-Pt/TiO$_2$ catalysts*, Chem. Eur. J., 16 7368-7371 (2010).

* cited by examiner

*Primary Examiner* — Paul A Zucker
(74) *Attorney, Agent, or Firm* — Stinson Leonard Street LLP

(57) ABSTRACT

A process for producing lactic acid from glycerol using a reaction mixture comprising glycerol, a dehydrogenation catalyst (preferably a copper-based catalyst), an alkaline component, and water.

17 Claims, 1 Drawing Sheet

CATALYST SYSTEM AND PROCESS FOR CONVERTING GLYCEROL TO LACTIC ACID

CROSS-REFERENCE TO RELATED APPLICATIONS

This application is based on and claims priority to U.S. Provisional Application Ser. No. 61/469,417, filed on Mar. 30, 2011, which is incorporated by reference in its entirety.

STATEMENT REGARDING FEDERALLY SPONSORED RESEARCH OR DEVELOPMENT

Not applicable.

BACKGROUND OF THE INVENTION

Global bio-diesel production by transesterification of fatty acid esters has increased by several folds in the last decade to partly substitute the use of fossil-derived diesel fuel. The byproduct, glycerol, in this process has emerged as an important building block for chemicals. For example, glycerol can be converted to several high value chemicals such as 1,2-propanediol, 1,3-propanediol, acrolein, and glyceric acid. Recently, lactic acid has emerged as another promising product from glycerol. Lactic acid (2-hydroxypropionic acid) is a platform chemical for several important commodity products such as biodegradable fibers, polylactic acid esters, and acrylic acid. Lactic acid is mainly produced (about 95% of world production) from sugars and sugar alcohols by the fermentation route which is slow and involves complex separation steps. See Datta, in Kirk-Othmer concise encyclopedia of chemical technology, Fifth ed., Vol. 1, Wiley-Interscience, NJ, 1324-1327 (2004).

Synthesis of lactic acid from glycerol has been described under oxygen flow conditions using an Au—Pt/$TiO_2$ catalyst and 4:1 molar ratio of NaOH to glycerol. The prior art reports high selectivity (86%); however, it uses oxygen and relatively high molar ratios of NaOH to glycerol. See Shen et al., *Efficient synthesis of lactic acid by aerobic oxidation of glycerol on Au—Pt/TiO2 catalysts*, Chem. Eur. J., 16 7368-7371 (2010). The abstract of Liu et al., *Method and special catalyst for production of lactic acid by using glycerol as raw material*, Chinese Patent No. 101695657 A (2010) describes a process which uses oxygen, alkali and a catalyst. The formation of lactic acid from glycerol using a high pressure of hydrogen (40-60 bar), base and a heterogeneous catalyst has also been described in Maris et al., *Glycerol hydrogenolysis on carbon-supported PtRu and AuRu bimetallic catalysts*, J. Catal. 251 281-294 (2007) and Marincean et al., *Glycerol hydrogenolysis to propylene glycol under heterogeneous conditions*, Chemical Industries 115 (Catalysis of Organic Reactions), 427-436 (2007). The major limitations are the use of hydrogen at high pressure and the low selectivity to lactic acid (40-60%).

Hydrothermal conversion of glycerol to lactic acid, wherein aqueous glycerol is treated at high temperature (573 K) under alkaline conditions, has been investigated as an alternative to the fermentation route. See Kishida et al., *Electrolysis of glycerol in subcritical water*, Chem. Lett. 34 1560-1561 (2005); Enomoto et al., U.S. Pat. No. 7,829,740 and 20100047140, which are all incorporated by reference in their entirety. The hydrothermal conversion process is advantageous as it can directly use glycerol from the bio-diesel production process containing water and alkali as feedstock with no need for a separation step. However, this process operates at near-critical temperature for water ($T_c$=647 K), and the alkaline medium therefore causes severe corrosion of the reactors. See Shen et al., *Effect of Alkaline Catalysts on Hydrothermal Conversion of Glycerin into Lactic Acid*, Ind. Eng. Chem. Res. 48 8920-8925 (2009), which is incorporated by reference.

The reaction pathway for glycerol to lactic acid is shown below. Dehydrogenation of glycerol to glyceraldehyde is a key step in this reaction. It has been shown that high temperatures (greater than 550 K) are required in the hydrothermal process to convert glycerol to glyceraldehyde via glyceroxide ion as an intermediate. Ramî rez-Ló pez et al., *Synthesis of lactic acid by alkaline hydrothermal conversion of glycerol at high glycerol concentration*, Ind. Eng. Chem. Res. 49 (14) 6270-6278 (2010). However, the decomposition of pyruvaldehyde and lactic acid are significant at that temperature, adversely affecting the selectivity to lactic acid.

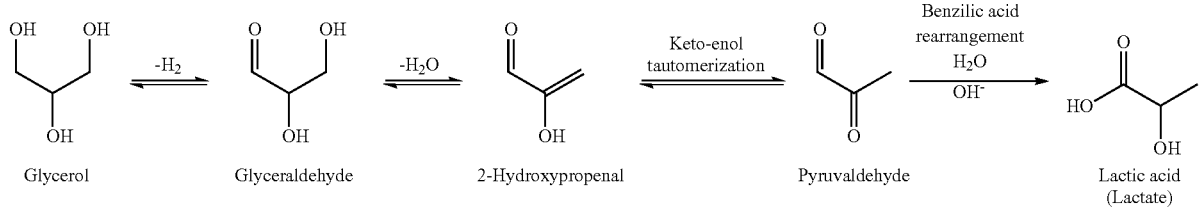

BRIEF SUMMARY OF THE INVENTION

The present invention is directed to a novel reaction mixture and novel process for converting glycerol to lactic acid. In the present invention, the reaction mixture comprises glycerol, an alkaline component, water, and a dehydrogenation catalyst. It is theorized that the dehydrogenation catalyst is used to facilitate conversion of glycerol to glyceraldehyde at relatively low temperatures. The alkaline component, also present in the reaction mixture, converts the glyceraldehyde to lactic acid.

In one aspect, the process of the present invention is carried out at a temperature of about 250° C. In yet another aspect, the process is carried out at a temperature between about 180 to 240° C.

In another aspect, the dehydrogenation catalyst used in the reaction mixture and process of the present invention is a copper-containing catalyst. For example, the dehydrogenation catalyst may be selected from the group consisting of metallic Cu, cuprous oxide ($Cu_2O$), cupric oxide (CuO), and copper chromite ($Cu_2Cr_2O_5$).

In another aspect, the dehydrogenation catalyst used in the reaction mixture and process of the present invention is a Raney catalyst. For example, the Raney catalyst may be selected from the group consisting of a Raney nickel catalyst or Raney cobalt catalyst.

In another aspect, the dehydrogenation catalyst used in the reaction mixture and process of the present invention comprises a metal selected from the group consisting of nickel, cobalt, copper, platinum, palladium, ruthenium, rhodium, and mixtures thereof. In still another aspect, the dehydrogenation catalyst is supported on a support selected from the group consisting of carbon, silica, aluminas, titania, zirconia, and zeolites.

In a further aspect, the reaction mixture of the present invention contains no added hydrogen or oxygen. Thus, in one aspect, the reaction process is carried out without adding hydrogen or oxygen.

In yet another aspect, the alkaline component of the reaction mixture is an alkali, alkaline earth metal hydroxide, or solid base. Likewise, the process of the present invention comprises use of an alkaline component which is an alkali, alkaline earth metal hydroxide, or solid base. In an exemplary aspect, the alkaline component to glycerol molar ratio ranges between about 0.5 to 7. In another exemplary aspect, the glycerol concentration ranges between about 10-50 wt % of the liquid in the reaction system.

In another aspect, the reaction mixture of the present invention has a pressure of about 10 to 50 bar. Likewise, the process may be carried out at a pressure of about 10 to 50 bar.

In still another aspect, the glycerol used in the reaction mixture and process is produced from plant fats, animal fats, or biomass.

In yet a further aspect, the dehydrogenation catalyst comprises a copper dehydrogenation catalyst and the process has a selectivity for lactic acid above about 60%. In another aspect, the selectivity is above about 65%. In still another aspect, the selectivity for lactic acid is above about 70%. In still another aspect, the selectivity is above about 75%.

In yet a further aspect, the dehydrogenation catalyst comprises a copper dehydrogenation catalyst and the process has glycerol conversion above about 60%. In another aspect, the glycerol conversion is above about 65%, 70%, 75%, 80%, 85%, 90%, or above about 95%. In another aspect, the conversion ranges between about 60% to 99%, more preferably about 70% to 99%, and still more preferably about 80% to 99%.

In yet a further aspect, the dehydrogenation catalyst comprises a Raney nickel catalyst or Raney copper catalyst and the process has a selectivity for a lactic acid above about 10%. In another aspect, the selectivity for lactic acid is above about 20%, 25%, 30%, 35%, 40%, or above about 45%. In still another aspect, the selectivity for lactic acid ranges from about 20% to 50%.

In yet a further aspect, the dehydrogenation catalyst comprises a Raney nickel catalyst or Raney copper catalyst and in the process has a glycerol conversion above about 80%. In another aspect, the glycerol conversion is above about 65%, 70%, 75%, 80%, 85%, 90%, 95%, or even above about 97%. In another aspect, the conversion ranges between about 60% to 99%, more preferably about 70% to 99%, and still more preferably about 80% to 99%.

In yet a further aspect, the dehydrogenation catalyst comprises a platinum catalyst and the process has a selectivity for a lactic acid above about 20%. In another aspect, the selectivity for lactic acid is above about 20%, 25%, 30%, 35%, 40%, 45%, or above about 50%. In another aspect, the selectivity for lactic acid ranges from about 20% to 60%.

In yet a further aspect, the dehydrogenation catalyst comprises a platinum catalyst and in the process has a glycerol conversion above about 40%. In another aspect, the glycerol conversion is above about 50%, 55%, 60%, 65%, 70%, 75%, 80%, 85%, 90%, 95%, or even above about 97%. In another aspect, the conversion ranges between about 60% to 99%, more preferably about 70% to 99%, and still more preferably about 80% to 99%.

In yet a further aspect, the dehydrogenation catalyst comprises a ruthenium catalyst and the process has a selectivity for a lactic acid above about 20%. In another aspect, the selectivity for lactic acid is above about 20%, 25%, 30%, 35%, or above about 40%. In another aspect, the selectivity for lactic acid ranges about 20% to 50%.

In yet a further aspect, the dehydrogenation catalyst comprises a ruthenium catalyst and in the process has a glycerol conversion above about 30%. In another aspect, the glycerol conversion is above about 30%, 35%, 40%, 45%, 50%, 55%, 60%, 65%, 70%, 75%, 80%, 85%, 90%, 95%, or even above about 97%. In another aspect, the conversion ranges between about 60% to 99%, more preferably about 70% to 99%, and still more preferably about 80% to 99%.

In yet a further aspect, the dehydrogenation catalyst comprises a palladium catalyst and the process has a selectivity for a lactic acid above about 20%. In another aspect, the selectivity for lactic acid is above about 20%, 25%, 30%, 35%, or above about 40%. In another aspect, the selectivity for lactic acid ranges about 20% to 50%.

In yet a further aspect, the dehydrogenation catalyst comprises a palladium catalyst and in the process has a glycerol conversion above about 30%. In another aspect, the glycerol conversion is above about 30%, 35%, 40%, 45%, 50%, 55%, 60%, 65%, 70%, 75%, 80%, 85%, or even above about 90%. In another aspect, the conversion ranges between about 60% to 99%, more preferably about 70% to 99%, and still more preferably about 80% to 99%.

In yet a further aspect, the dehydrogenation catalyst comprises a rhodium catalyst and the process has a selectivity for a lactic acid above about 20%. In another aspect, the selectivity for lactic acid is above about 20%, 25%, 30%, 35%, or above about 40%. In another aspect, the selectivity for lactic acid ranges about 20% to 50%.

In yet a further aspect, the dehydrogenation catalyst comprises a rhodium catalyst and in the process has a glycerol conversion above about 30%. In another aspect, the glycerol conversion is above about 30%, 35%, 40%, 45%, 50%, 55%, 60%, 65%, 70%, 75%, 80% or even above about 85%. In another aspect, the conversion ranges between about 60% to 99%, more preferably about 70% to 99%, and still more preferably about 80% to 99%.

The present invention demonstrates for the first time that the synthesis of lactic acid from glycerol may be achieved using a dehydrogenation catalyst (e.g., a copper catalyst) along with a base without the necessity of using either a reductant or oxidant. The proposed catalyst system and process gives high yields at lower temperatures (e.g., typically about 473-513 K) compared to the known hydrothermal route in the prior art. Further, as discussed above, the prior art methods either use hydrogen or oxygen along with a catalyst and high concentration of a base (8:1 to 4:1 molar ratio of NaOH/glycerol), or high temperature (553-573 K, hydrothermal route) and moderate concentrations of base (1.1:1 to 1.6:1 molar ratio of NaOH/glycerol).

The use of a dehydrogenation catalyst (e.g., copper catalyst) along with the alkaline component (e.g., NaOH) is a promising one-pot, low temperature route for glycerol conversion to lactic acid. The present invention is significant as the previous reports on metal catalyzed conversion of glycerol to lactic acid employ Pt, Ru, PtRu, AuRu catalysts and require either oxygen or hydrogen with higher alkali concentration (molar alkali/glycerol molar ratios between 4 and 8).

See Shen et al., *Efficient Synthesis of Lactic Acid by Aerobic Oxidation of Glycerol on Au—Pt/TiO₂ Catalysts*, Chem. Eur. J. 16 7368-7371 (2010); Maris et al., *Hydrogenolysis of Glycerol over Carbon-Supported Ru and Pt Catalysts*, J. Catal. 249 328-337 (2007); Maris et al., *Glycerol Hydrogenolysis on Carbon-Supported PtRu and AuRu Bimetallic Catalysts*, J. Catal. 251 281-294 (2007); and Marincean, S.; Peereboom, L.; Xi, Y.; Miller, D. J.; Jackson, J. E., Chemical Industries, 115 427-436 (2007).

As discussed in more detail below, generally speaking, the process of the present invention results in high conversions of glycerol and high selectivities to lactic acid under milder and greener reaction conditions and is the first report using dehydrogenation catalysts without using reducing or oxidizing agents.

Lactic acid is industrially manufactured from sugars and sugar alcohols by a fermentation route which is very slow (4-6 days) and produces lactic acid in low concentrations (less than 10 wt %) requiring complex multistep separation. Glycerol can be used as a cheap and renewable feedstock for producing lactic acid. This chemocatalytic route is much faster (4-6 hours) than the fermentation route yielding higher product concentration at significantly lower temperatures compared to the hydrothermal route without compromising to the yields. In this chemocatalytic route, the use of oxidative or reductive environment is eliminated unlike the prior art reports.

The proposed process has great potential for converting glycerol to lactic acid efficiently under milder reaction conditions achieved by using a new supported/unsupported metal catalyst. Lactic acid can be further converted to acrylic acid (an important commodity product) by catalytic dehydration, thus providing a production route based on renewable feedstock.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
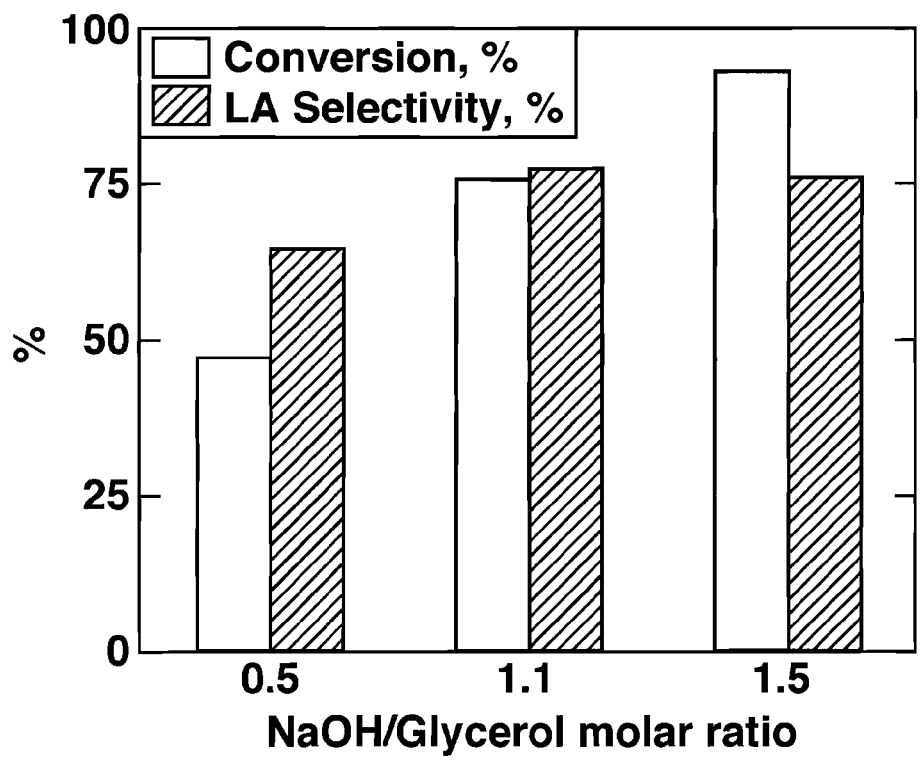
FIG. 1 shows the effect of NaOH/glycerol molar ratio on lactic acid formation. Reaction conditions: glycerol:3 g; Cu/SiO₂:0.4 g; $P_{N2}$:14 bar; 513 K; solvent:H₂O; initial liquid volume: 30 ml; batch reaction time: 6 hours.

The present invention is directed to a reaction mixture and process for producing lactic acid from glycerol. The process comprises forming a reaction mixture comprising glycerol, an alkaline component, a dehydrogenation catalyst, and water. The reaction mixture undergoes a catalytic reaction, preferably in a stirred reactor. The process preferably is conducted in the absence of either additional hydrogen or oxygen as required in the prior art processes. Moreover, the process preferably occurs at a temperature that is lower (typically about 80 to 100° C. lower) than the hydrothermal conversion processes of the prior art, such as that disclosed in Enomoto et al., U.S. Pat. No. 7,829,740, which is incorporated by reference.

In one aspect of the process according to the invention, glycerol may be obtained from plant fats, animal fats, biomass, or the like, or pure product synthesized chemically is preferably used as a starting material. The raw material comprising glycerol may be obtained in the production of diesel fuel oil from fats. The fats are subjected to transesterification with alcohol in the presence of an alkaline catalyst in order to obtain the fatty acid ester. The concentration of glycerol in the reaction mixture is typically in the range of 1 to 100% by weight (e.g., about 1, 10, 20, 30, 40, 50, 60, 70, 80, 90, or 100 wt % or some range therebeween).

The dehydrogenation catalysts used in the reaction mixture and process of the present invention are not particularly limited. The catalysts are typically solid catalysts containing one or more metal elements such as Ba, Co, Cr, Cu, Fe, Mn, Ni, Pd, Pt, Zn, Zr, Ru, and Rh. The metal elements may be used in the form of, for example, metallic elemental substances, alloys, oxides, salts, or complexes. Dehydrogenation catalysts, such as Raney catalysts, may also be used. The dehydrogenation catalysts may be used singly, or two or more kinds may be used in combination. For example, the dehydrogenation catalyst may be a mixture of metallic elemental substances, a mixture of a metallic elemental substance and a metal oxide, a mixture of metal oxides, or a mixed metal oxide. Further, the catalyst employed may be in either the reduced or unreduced form. The reduced forms of the catalysts may have a more uniform distribution of active sites and may be more active for the catalytic transformations.

In one aspect, the preferred metal elements comprising the dehydrogenation catalyst are selected from the group consisting of one or more of Ni, Co, Cu, Pd, Pt, Ru, and Rh.

In another aspect, a Raney catalyst is used as the dehydrogenation catalyst in the reaction. The Raney catalysts in the invention are generally metal catalysts that are obtained by alloying a metal which is insoluble in alkali or acid, e.g., nickel, cobalt, copper or iron, with a metal which is soluble in alkali or acid, e.g., aluminum, silicon, zinc, or magnesium, and thereafter dissolving the alkali- or acid-soluble metal from the alloy. Examples of the Raney catalysts include Raney nickel catalysts, Raney cobalt catalysts, Raney copper catalysts, and Raney iron catalysts. In one aspect, the Raney catalyst is selected from the group consisting of Raney nickel catalysts and Raney cobalt catalysts.

In one aspect, the dehydrogenation catalyst comprises a copper catalyst. Exemplary copper catalysts include elemental copper as well as salts, oxides, alloys, and complexes thereof Exemplary oxygen-containing copper catalysts include cuprous oxide (Cu₂O), cupric oxide (CuO), copper chromite (Cu₂Cr₂O₅)., and mixtures thereof. In another aspect, the copper catalyst is a copper salt, including but not limited to copper salts having nitrogen-containing anions such as copper nitrate, copper nitrite, copper nitride, copper cyanide, copper ferrocyanide; copper salts having halogen-containing anions, such as copper chloride, copper bromide, copper perchlorate, copper bromate, and copper iodide; copper salts having sulfur containing anions, such as, copper sulfide, copper sulfate, and copper thiocyanate; copper salts having organic carboxylic acid containing anions, such as copper carbonate, copper formate, copper acetate, copper oxalate, copper butyrate, copper citrate, copper benzoate; and other copper salts such as copper borate, copper phosphate, copper carbide, copper chromate, and copper tungstate, and mixtures thereof Other exemplary copper catalysts include copper chromite, bis[copper (I) trifluoromethanesulfonate], benzene complex (i.e., copper (I) triflate), copper (II) trifluoromethanesulfonate (i.e., copper (II) triflate), copper (I) bromide (most conveniently as a stabilized complex, such as copper (I) bromide-dimethylsulfide complex), cupric tetrafluoroborate, and cuprous benzoate. Mixtures of any of the foregoing are also contemplated within the present invention.

In one aspect, the dehydrogenation catalyst comprises a ruthenium catalyst. Exemplary ruthenium catalysts include elemental ruthenium as well as salts, oxides, alloys, and complexes thereof. For example, the ruthenium catalyst may be selected from the group consisting of ruthenium halides (e.g., fluoride, chloride), ruthenium nitrate, ruthenium nitride, ruthenium carboxylates (e.g., acetate, propionate, butyrate, valerate, benzoate, octanoate), ruthenium hydroxide, and ruthenium sulfite. Other examples include ruthenium phosphines, such as dichlorotris(triphenylphosphine)ruthenium and carbonylbistrifluoroacetatebis (triphenylphosphine)ruthenium, $HRh(PPh_3)_4$, $H_2 Ru(PPh_3)_4$, and $RhCl(PPh_3)_3$. Mixtures of any of the foregoing are also contemplated within the present invention.

In one aspect, the dehydrogenation catalyst comprises a palladium catalyst. Exemplary palladium catalysts include elemental palladium, as well as salts, oxides, alloys, and complexes thereof Examples of the palladium catalysts include organic acid salts such as palladium acetate and palladium cyanate; halides such as palladium fluoride, palladium chloride, palladium fluoride and palladium iodide; oxo-acid salts such as palladium nitrate and palladium sulfate; palladium oxide; palladium hydroxide; and complexes such as dichlorocyclooctadienepalladium, dichloronorbornadienepalladium, tetrakisacetonitrilepalladium tetrafluoroborate, tetrakisbenzonitrilepalladium di-tetrafluoroborate, dichlorobisacetonitrilepalladium, dichlorobisethylenediaminepalladium, bisacetylacetonatopalladium, tris-triphenylphosphineacetonitrilepalladium tetrafluoroborate, dichlorobistriethylphosphinepalladium, dichlorobis-(dimethylsulfide)palladium, dibenzoylsulfidepalladium, bis(2,2'-bipyridine)palladium perchlorate, and tetrakis-(pyridine)palladium dichloride. Mixtures of any of the foregoing are also contemplated within the present invention.

In one aspect, the dehydrogenation catalyst comprises a rhodium catalyst. Exemplary rhodium catalysts include elemental rhodium, as well as salts, oxides, alloys, and complexes thereof. Examples of rhodium catalysts include mentioned halides such as rhodium chloride, rhodium bromide and rhodium iodide; inorganic acid salts such as rhodium nitrate and rhodium sulfate; organic acid salts such as rhodium acetate, rhodium formate, rhodium propionate, rhodium butyrate, rhodium valerate and rhodium naphthenate; rhodium oxide, rhodium trihydroxide; and complexes such as dichloro-bis(triphenylphosphine) rhodium, trichloro-tris-pyridinerhodium, tetrarhodium dodecacarbonyl, dirhodium octacarbonyl, hexarhodium hexadecarbonyl, rhodium dicarbonylacetylacetonate, rhodium carbonyl(1-phenylbutane-1,3-dion), tris(hexane-2,4-dion)rhodium, tris (heptane-2,4-dion)rhodium, tris(1-phenylbutane-1,3-dion) rhodium, tris(3-methylpentane-2,4-dion)rhodium, and tris(1-cyclohexylbutane-1,3-dion)rhodium. Mixtures of any of the foregoing are also contemplated within the present invention.

In one aspect, the dehydrogenation catalyst comprises a platinum catalyst. Exemplary platinum catalysts include elemental platinum as well as salts, oxides, alloys, and complexes thereof similar to the other platinum group metals discussed above. Mixtures of any of the foregoing are also contemplated within the present invention.

Other examples of possible dehydrogenation catalysts for use in the invention include mixtures of the foregoing metals, for example copper-chromium catalysts such as $CuO$—$Cr_2O_3$—$BaO$ and $CuO$—$Cr_2O_3$—$BaO$—$MnO$, copper-zinc catalysts such as $CuO$—$ZnO$, zinc-chromium catalysts such as $ZnO$—$Cr_2O_3$, palladium-chromium catalysts such as $Pd$—$Cr_2O_3$, cobalt-zirconium catalysts such as $CoO$—$ZrO_2$, nickel-zirconium catalysts such as $Ni$—$ZrO_2$, and nickel-magnesium catalysts such as $Ni$—$MgO$.

The catalyst maybe supported or unsupported. Suitable support materials may include, for example, stable metal oxide-based supports or ceramic-based supports as well as molecular sieves, such as zeolites. Examples of suitable support materials include without limitation, iron oxide, silica, alumina, titania, zirconia, magnesium oxide, calcium silicate, carbon, graphite, high surface area graphitized carbon, activated carbons, clays, and mixtures thereof. Exemplary preferred supports are selected from the group consisting of carbon, silica, aluminas, titania, zirconia, and basic zeolites. The total weight of the support in the catalyst, based on the total weight of the catalyst, is typically about 5 wt % to 99 wt % (e.g., about 5, 10, 15, 20, 25, 30, 35, 40, 45, 50, 55, 60, 65, 70, 75, 80, 85, 90, 95, or 99 wt %).

In one aspect, the alkaline component is selected from the group consisting of hydrides of alkali metals or alkaline earth metals (e.g., lithium hydride, sodium hydride, potassium hydride, calcium hydride, etc.), amides of alkali metals or alkaline earth metals (e.g., lithium amide, sodium amide, lithium diisopropylamide, lithium dicyclohexylamide, lithium hexamethyldisilazide, sodium hexamethyldisilazide, potassium hexamethyldisilazide, etc.), lower alkoxides of alkali metals or alkaline earth metals (e.g., sodium methoxide, sodium ethoxide, potassium tert-butoxide, etc.). In yet another example, inorganic bases such as hydroxides of alkali metals or alkaline earth metals (e.g., sodium hydroxide, potassium hydroxide, lithium hydroxide, barium hydroxide, calcium hydroxide, etc.), carbonates of alkali metals or alkaline earth metals (e.g., sodium carbonate, potassium carbonate, cesium carbonate, etc.), hydrogencarbonates of alkali metals or alkaline earth metals (e.g., sodium hydrogencarbonate, potassium hydrogencarbonate, etc.), and basic zeolites may be used. In still another example, amines such as triethylamine, diisopropylethylamine, N-methylmorpholine, dimethylaminopyridine, as well as organic bases such as basic heterocyclic compounds (e.g., pyridine and imidazole) may be used. The molar ratio of glycerol to the base ranges from about 0.3 to 7.0 (e.g., about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, or 7.0 or some range therebetween), with molar ratios of about 0.5 to 1.5 being most preferred.

In one aspect, the temperature of the reaction is preferably maintained below about 250° C., for example less than about 245° C., 240° C., 235° C., 230° C., 225° C., 220° C., 215° C., 210° C., 205° C., 200° C., 195° C., 190° C., 185° C., 180° C., 175° C., 170° C., 165° C., 160° C., 155° C., or 150° C. (or some range therebetween such values). In still another aspect, the temperature of the reaction is preferably conducted between about 150 and 250° C., with temperatures of about 160 to 240° C. being most preferred.

In one aspect, the pressure of the reaction is preferably about 10 to 300 bar, with pressures of about 10 to 100 bar being most preferred (e.g., about 10, 15, 20, 25, 30, 35, 40, 45, 50, 55, 60, 65, 70, 75, 80, 85, 90, 95, or 100 bar or some range therebetween).

The process of the present invention is preferably carried out in corrosion resistant reactors and other equipment. Preferred corrosion resistant materials include teflon lined or glass lined vessels.

In the present invention, the conversion of glycerol is preferably greater than about 20%. Exemplary glycerol conversions are above about 25%, 30%, 35%, 40%, 45%, 50%, 55%, 60%, 65%, 70%, 75%, 80%, 85%, 90%, 95%, 96%, 97%, 98%, and even about 99% (or have some range therebetween).

In the present invention, the selectivity for lactic acid is preferably greater than 20%. Exemplary selectivities are greater than about 25%, 30%, 35%, 40%, 45%, 50%, 55%, 60%, 65%, 70%, 75%, or even greater than about 80% (or some range therebetween).

The processes of the present invention may be performed in either batch or continuous mode. Typically, the reaction is allowed to proceed for about 0.5 to 10 hours (e.g., about 0.5, 1, 1.5, 2, 2.5, 3, 3.5, 4, 4.5, 5, 5.5, 6, 6.5, 7, 7.5, 8, 8.5, 9, 9.5, or 10 hours or some range therebetween).

It will be appreciated that the reaction product comprises an alkaline solution containing lactic acid, which can be efficiently concentrated using an electrodialysis unit. Further, the alkaline solution containing lactic acid can be separated into lactic acid and alkaline component according to a separator, for example one with a bipolar membrane. Still furthermore, solid lactate salt may be separated from the alkylene component according to a crystallization process. The unreacted glycerol dissolved in the solution comprising the alkaline component may also be recovered in order to reuse the recovered glycerol as a raw material. Such steps are generally disclosed in Enomoto et al., U.S. Pat. No. 7,829,740 and Published Patent Application No. 2010/0047140, which are incorporated by reference.

For example, in the process for producing lactic acid from glycerol according to the present invention, a solution containing glycerol, the alkaline component, and water may be continuously fed into a reactor containing the dehydrogenation catalyst. The process may use conventional equipment, such as a high-pressure pump, a pre-heater, a reactor, a cooler, and a storage tank for storing the reaction products (i.e., the alkaline solution comprising lactic acid and other byproducts). The pre-heater may be used preliminarily to heat the alkaline solution containing glycerol before it is introduced in a reactor where the reaction is carried out under a high temperature and high pressure conditions in the presence of the dehydrogenation catalyst. In the reactor, the alkaline solution containing glycerol and dehydrogenation catalyst are subjected to elevated temperatures and pressures to convert the glycerol in the alkaline solution to lactic acid. The reaction products may be cooled by the cooler, and then the resultant alkaline solution comprising lactic acid and other byproducts may be transported to the storage tank. One or more valves may be used to release and control the pressure in the reactor and/or storage tank.

The reaction product which contains lactic acid may be concentrated using an electrodialysis unit. Furthermore, the alkaline solution comprising the lactic acid can be separated into lactic acid and alkaline component using a separator with a bipolar membrane. Still furthermore, if it is desirable, lactic acid and a salt of the alkaline component can be removed as a solid from the reaction product (the alkaline solution containing lactic acid) using a crystallizer.

The following examples are presented to demonstrate the present invention and to illustrate certain specific embodiments thereof These examples should not be construed to limit the scope of the invention as set forth in the claims. There are many other possible variations, as those of ordinary skill in the art will recognize, which are within the spirit of the invention.

EXAMPLE 1

Effect of Reactor Construction Material

It is well documented in the literature that NaOH leads to leaching of reactor construction materials. Further, the leached metals may catalyze chemical transformations. To investigate such a possibility, three reactions with an aqueous solution containing NaOH and glycerol (without Cu-catalysts) were conducted in different reactors; one made of Hastelloy-C, one of titanium, and the third with a teflon liner inside the reactor to avoid contact of the reaction mixture with the reactor wall. The experiment in the Hastelloy-C reactor showed 36.4% glycerol conversion with 90.1% selectivity to lactic acid after 6 hours at 473 K. ICP analysis of the reaction mixture showed the presence of Fe (less than 7 ppm), Cr (less than 5 ppm), and Ni (less than 3 ppm). The titanium reactor showed very low conversion (5%), but suffered significant corrosion. In sharp contrast, the teflon-lined reactor showed negligible conversion (0.26%) under identical conditions. These experiments clearly indicate that leached metals catalyze glycerol conversion in the Hastelloy-C reactor. Therefore, further experiments were conducted in a teflon lined reactor.

EXAMPLE 2

Dehydrogenation Catalysts

This example investigates the catalytic effects of various dehydrogenation catalysts on glycerol conversion to lactic acid under alkaline conditions. The experiments involved copper-containing catalysts (Cu, CuO, $Cu_2O$, and copper chromite), activated base metal catalysts (Raney Ni and Raney Co), and precious metal catalysts (Pt, Pd, Ru, and Rh). Precious metal catalysts are all with 5% (w/w) metal loading and supported on activated carbon.

In the experiments described below, the following materials were used. Glycerol (purity greater than or equal to 99.5%), $Cu_2O$ in powder form, and 13 wt % $CuO/Al_2O_3$ were purchased from Sigma-Aldrich. 60 wt % $Cu/SiO_2$ was supplied by Evonik Degussa and powdered (to 100-125 µm) before use. The other supported metal catalysts and Raney cobalt catalysts investigated were also purchased from Sigma-Aldrich. The Raney nickel catalyst was purchased from Grace Davison. Hydrogen (greater than 99.5%) and nitrogen (greater than 99%) were procured from Air Gas Inc. and Linweld, respectively.

The reactions were conducted in a high temperature; high pressure multiple batch slurry reactor setup. See Roy et al., *Aqueous phase hydrogenolysis of glycerol to 1,2-propanediol without external hydrogen addition*, Catal. Today 156 (1-2), 31-37 (2010), which is incorporated by reference. For the reactions with $Cu/SiO_2$ catalyst, the catalyst was activated inside the reactor at 513 K and 70 bar partial pressure of $H_2$ for 12 hours. After the activation the reactor was cooled down, $H_2$ was released and the reactor was purged three times with $N_2$. A known amount of glycerol and NaOH dissolved in a predetermined volume of water was injected into the reactor. The reactor was purged three times with $N_2$. The reactor was heated to a desired temperature; $N_2$ was introduced into the reactor up to 14 bar and reaction started by increasing agitation speed to 9 Hz. $N_2$ pressurization allows easy and adequate sampling of the gas phase for GC analysis at the end of the run. At the end of the run, the reactor was cooled and the reactor pressure was noted. The gas phase sample was analyzed offline by GC. See Torres et al., *Kinetic Modeling of Aqueous-Phase Glycerol Hydrogenolysis in a Batch Slurry Reactor*, Ind. Eng. Chem. Res. 49 10826-10835 (2010), which is incorporated by reference. The reactor was opened, and the pH of the reaction mixture was measured. Liquid phase sample for analysis was prepared by diluting the reaction mixture with 20 ml aqueous $H_2SO_4$ solution to lower the pH of the HPLC sample to less than or equal to 7 as the HPLC column used in the analysis is unsuitable for basic samples. The final volume and pH of the mixture was noted. Part of the liquid sample was passed through syringe filters and analyzed by HPLC. See Tones et al., *Kinetic Modeling of Aqueous-Phase Glycerol Hydrogenolysis in a Batch Slurry Reactor*, Ind. Eng. Chem. Res. 49 10826-10835 (2010). Calibrations for glycerol and the expected gas and liquid phase products were performed for quantitative analysis. The analytical procedure is able to account for about 90% of the starting glycerol. It is important to note that carbonate can form during the reaction and is indirectly confirmed by the bubbles ($CO_2$) formed when the reaction mixture was diluted with aqueous $H_2SO_4$ solution.

For the reactions with $Cu_2O$ or $CuO/Al_2O_3$, the catalyst was used as received. For these reactions, the catalyst, dissolved glycerol, and NaOH in water were charged into the reactor, the reactor was sealed, and the experiment was conducted as described above.

EXAMPLE 2A

Cu/SiO$_2$, Cu$_2$O and Cu/Al$_2$O$_3$ Catalyst

To investigate the hypothesis that a good dehydrogenation catalyst and alkali can convert glycerol to lactic acid at lower temperatures compared to the hydrothermal process, three different copper catalysts (viz. Cu/SiO$_2$, Cu$_2$O, and Cu/Al$_2$O$_3$) were tested and the results are shown in Table 1. CuO and Cu$_2$O catalysts showed higher conversion (about 95%) of glycerol than Cu/SiO$_2$ catalyst (75%) with identical lactic acid selectivity (75-80%) at a significantly lower temperature compared to hydrothermal synthesis, and also without the need for a reductant (hydrogen) or an oxidant (oxygen). The silica and alumina supports are known to leach out under alkaline conditions and high temperature forming sodium silicate (Na$_2$SiO$_3$) and aluminates (e.g., NaAlO$_2$), respectively. See Sarkar, *The removal of alumina and silica from iron rejects slime by chemical leaching*, Hydrometallurgy 105 364-369 (2011). Such a problem clearly does not exist with the unsupported Cu$_2$O catalyst.

TABLE 1

Comparison of different Cu-based catalysts

|  | Cu/SiO$_2$ | CuO/Al$_2$O$_3$ | Cu$_2$O |
|---|---|---|---|
| Glycerol conversion, % | 75.2 | 97.8 | 93.6 |
| Liquid phase product selectivity, % | | | |
| Glyceraldehyde | 0.43 | 0.01 | 0.03 |
| Pyruvaldehyde | 0.03 | 0.02 | 0.00 |
| Ethylene glycol | 0.39 | 0.00 | 0.32 |
| 1,2-Propanediol | 2.15 | 1.54 | 6.03 |
| Lactic acid | 79.7 | 78.6 | 78.1 |
| Acetic acid | 2.61 | 1.33 | 1.90 |
| Formic acid | 0.13 | 0.02 | 0.15 |
| Methanol | 5.15 | 0.72 | 0.69 |

TABLE 1-continued

Comparison of different Cu-based catalysts

|  | Cu/SiO$_2$ | CuO/Al$_2$O$_3$ | Cu$_2$O |
|---|---|---|---|
| Ethanol | 0.52 | 0.00 | 0.53 |
| Propanol | 0.00 | 0.00 | 0.00 |
| Gas phase product selectivity, % | | | |
| Methane | 0.90 | 1.04 | 3.86 |
| Ethane | 0.01 | 0.02 | 0.04 |
| Propane | 0.00 | 0.02 | 0.03 |
| Butane | 0.01 | 0.05 | 0.11 |

Reaction conditions: glycerol: 3 g; NaOH/glycerol molar ratio: 1.1; Cu: 3.5 mmol; $P_{N2}$: 14 bar; 513 K; solvent: $H_2O$; initial liquid volume: 30 ml; batch reaction time: 6 hours.

EXAMPLE 2B

Copper chromite (Cu$_2$Cr$_2$O$_5$) Catalyst

Copper chromite catalyst was tested in unreduced and reduced forms for glycerol conversion under alkaline condition. The results presented in Table 2 indicate that the conversion of glycerol is low (<25%) with about 65% selectivity to lactic acid in both the cases.

TABLE 2

Glycerol conversion under alkaline conditions using copper chromite catalyst

|  | Unreduced, 0.4 g | Reduced*, 1 g |
|---|---|---|
| Glycerol conversion, % | 20.23 | 23.52 |
| Liquid phase product selectivity, % | | |
| Glyceraldehyde | 1.44 | 3.11 |
| Pyruvaldehyde | 21.66 | 12.43 |
| Ethylene glycol | 0.00 | 0.83 |
| 1,2-Propanediol | 0.00 | 1.86 |
| Lactic acid | 63.54 | 66.51 |
| Acetic acid | 0.00 | 0.00 |
| Methanol | 0.00 | 0.00 |
| Ethanol | 0.00 | 0.00 |
| 2-Propanol | 0.00 | 0.00 |
| Gas phase product selectivity, % | | |
| Methane | 2.79 | 1.51 |
| Ethane | 0.09 | 0.03 |
| Propane | 0.02 | 0.02 |
| Butane | 0.05 | 0.02 |
| Pentane | 0.05 | 0.08 |

Reaction conditions: glycerol: 3 g; NaOH/glycerol molar ratio: 1.1; $P_{N2}$: 14 bar; Temperature: 493 K; solvent: $H_2O$; initial liquid volume: 30 ml; batch reaction time: 6 hours
*Catalyst reduced inside the reactor at 513 K and 100 bar partial pressure of hydrogen for 12 hours

EXAMPLE 2C

Raney Ni Catalyst

Raney Ni catalyst was investigated for glycerol conversion to lactic acid at various temperatures and the results are presented in Table 3. The Raney Ni catalysts were reduced inside the reactor at 513 K and 100 bar partial pressure of hydrogen for 6 hours prior to a batch reaction. The conversion of glycerol was near 100% in 6 hours even at 443 K and 87% at 423 K; however, selectivity to lactic acid was always poor. At higher temperatures, methane was the major product which decreased with temperature. At 423 K, methane selectivity reduced significantly and 1,2-PDO was observed as a major product (selectivity: 40.95%). This indicates that while reforming followed by methanation reaction is facilitated at higher temperatures with Raney Ni catalyst, hydrogenation (hydrogen generated in situ due to the formation of lactic acid and by reforming reaction) is predominant at lower temperatures.

TABLE 3

Glycerol conversion under alkaline conditions using Raney Ni catalyst

|  | 493 K, 3 g catalyst | 473 K, 1 g catalyst | 443 K, 1 g catalyst | 423 K, 1 g catalyst |
|---|---|---|---|---|
| Glycerol conversion, % | 99.30 | 98.49 | 95.66 | 86.95 |
| Liquid phase product selectivity, % | | | | |
| Glyceraldehyde | 0.28 | 0.31 | 0.30 | 0.00 |
| Pyruvaldehyde | 0.00 | 0.00 | 3.03 | 4.95 |
| Ethylene glycol | 0.00 | 0.00 | 1.82 | 3.75 |
| 1,2-Propanediol | 0.28 | 4.90 | 25.58 | 40.95 |
| Lactic acid | 7.38 | 19.92 | 18.01 | 20.30 |
| Acetic acid | 5.20 | 2.35 | 1.01 | 0.00 |
| Methanol | 0.00 | 1.43 | 0.76 | 0.00 |
| Ethanol | 0.57 | 2.96 | 4.94 | 3.87 |
| 2-Propanol | 0.00 | 0.00 | 0.00 | 0.00 |
| Gas phase product selectivity, % | | | | |
| Methane | 64.62 | 48.20 | 21.15 | 4.68 |
| Ethane | 2.29 | 2.09 | 7.51 | 0.44 |
| Propane | 0.56 | 0.04 | 1.17 | 0.07 |
| Butane | 0.01 | 0.00 | 0.01 | 0.00 |
| Pentane | 0.11 | 0.02 | 0.11 | 0.01 |

Reaction conditions: glycerol: 3 g; NaOH/glycerol molar ratio: 1.1; $P_{N2}$: 14 bar; solvent: $H_2O$; initial liquid volume: 30 ml; batch reaction time: 6 h.

EXAMPLE 2D

Raney Co Catalyst

Raney Co catalysts showed trends similar to that with Raney Ni for glycerol conversion under alkaline condition (Table 4). Raney Co catalysts were also reduced inside the reactor at 513 K and 100 bar partial pressure of hydrogen for 6 hours prior to a batch reaction. However, Raney Co was found to be less active for methane formation reaction and showed better selectivity to lactic acid (37-48%) over a range of temperature (423-493 K) compared to the Raney Ni catalyst. 1,2-PDO formation increased with decrease in temperature.

TABLE 4

Glycerol conversion under alkaline conditions using Raney Co catalyst

|  | 493 K, 3 g catalyst | 473 K, 1 g catalyst | 443 K, 1 g catalyst | 423 K, 1 g catalyst |
|---|---|---|---|---|
| Glycerol conversion, % | 98.87 | 96.90 | 95.82 | 94.40 |
| Liquid phase product selectivity, % | | | | |
| Glyceraldehyde | 0.29 | 0.34 | 0.44 | 1.60 |
| Pyruvaldehyde | 0.00 | 0.00 | 4.36 | 3.53 |
| Ethylene glycol | 0.00 | 0.71 | 0.29 | 0.96 |
| 1,2-Propanediol | 1.14 | 21.66 | 23.71 | 37.53 |
| Lactic acid | 37.55 | 39.36 | 47.56 | 44.48 |
| Acetic acid | 7.80 | 1.02 | 0.97 | 0.21 |
| Methanol | 0.86 | 3.81 | 3.59 | 0.53 |
| Ethanol | 0.95 | 1.83 | 1.45 | 0.00 |
| 2-Propanol | 0.00 | 0.00 | 0.29 | 0.00 |
| Gas phase product selectivity, % | | | | |
| Methane | 34.32 | 12.21 | 4.70 | 1.86 |
| Ethane | 0.82 | 0.28 | 1.02 | 0.40 |
| Propane | 0.41 | 0.19 | 0.78 | 0.34 |
| Butane | 0.08 | 0.01 | 0.02 | 0.01 |
| Pentane | 0.92 | 0.05 | 0.09 | 0.04 |

Reaction conditions: glycerol: 3 g; NaOH/glycerol molar ratio: 1.1; $P_{N2}$: 14 bar; solvent: $H_2O$; initial liquid volume: 30 ml; batch reaction time: 6 h.

EXAMPLE 2E

Platinum

Glycerol conversion under alkaline condition in the presence of Pt/C catalyst was studied at various temperatures and batch times and the product profiles are presented in Table 5. It is important to mention that, at 493 K, significant formation of $CO_2$ (converted to sodium carbonate under alkaline condition, hence not identified either by GC or HPLC) led to lower (70.5%) carbon based selectivity to the observed gas and liquid phase products (based on C balance). $CO_2$ formation was less at 463 K and almost negligible at 433 K. Lactic acid selectivity reached its maximum (54.14%) at 433 K for a 2 hour batch run; however, prolonged runs at that temperature reduced the selectivity to 25.84%. This is mainly due to the hydrogenation of either glyceraldehyde or lactic acid at this temperature using the hydrogen produced in situ. This is further supported by the results presented in Table 6, where these results are compared with externally added hydrogen in the reaction system to facilitate hydrogenation reactions. The conversion of glycerol is lower in the presence of externally added hydrogen, which may be due to the fact that glyceraldehyde formation is a dehydrogenation step and is less favored in the presence of excess hydrogen. Solubility of hydrogen in water (especially in alkaline water) is very low, which may explain why the conversion has not reduced significantly (10-15%) in the presence of externally added hydrogen. The selectivity to lactic acid and 1,2-PDO is affected significantly by the presence of externally added hydrogen and the effect is more pronounced in the 2 hour batch runs (reduced from 54.14% to 30.84% for lactic acid and increased from 20.85% to 53.77% for 1,2-PDO). These results indicate that lower reaction temperature and lower residence time are required for better selectivity to lactic acid with Pt catalyst. Lower selectivity to 1,2-PDO at higher temperatures (Table 5) may be due to significant reforming of 1,2-PDO with Pt catalyst at those temperatures.

TABLE 5

Glycerol conversion under alkaline condition using platinum (Pt) catalyst

|  | 493 K, 6 h | 463 K, 2 h | 463 K, 6 h | 433 K, 2 h | 433 K, 6 h |
|---|---|---|---|---|---|
| Glycerol conversion, % | 97.14 | 91.62 | 98.84 | 44.90 | 78.66 |
| Liquid phase product selectivity, % | | | | | |
| Glyceraldehyde | 0.29 | 0.00 | 0.15 | 0.34 | 0.18 |
| Pyruvaldehyde | 0.07 | 0.00 | 0.00 | 0.67 | 0.37 |

TABLE 5-continued

Glycerol conversion under alkaline condition using platinum (Pt) catalyst

|  | 493 K, 6 h | 463 K, 2 h | 463 K, 6 h | 433 K, 2 h | 433 K, 6 h |
|---|---|---|---|---|---|
| Ethylene glycol | 0.88 | 1.09 | 0.69 | 1.57 | 1.85 |
| 1,2-Propanediol | 9.59 | 12.75 | 11.76 | 20.85 | 36.54 |
| Lactic acid | 37.16 | 49.02 | 47.34 | 54.14 | 25.84 |
| Acetic acid | 3.34 | 1.42 | 1.37 | 0.00 | 1.23 |
| Methanol | 7.91 | 11.33 | 11.57 | 10.76 | 9.47 |
| Ethanol | 5.60 | 8.61 | 8.53 | 4.93 | 8.24 |
| 2-Propanol | 2.36 | 4.90 | 4.70 | 2.02 | 3.88 |
| Gas phase product selectivity, % | | | | | |
| Methane | 1.87 | 0.20 | 0.59 | 0.16 | 1.02 |
| Ethane | 0.43 | 0.10 | 0.11 | 0.09 | 0.27 |
| Propane | 0.81 | 0.18 | 0.18 | 0.06 | 0.68 |
| Butane | 0.01 | 0.01 | 0.00 | 0.00 | 0.00 |
| Pentane | 0.01 | 0.16 | 0.10 | 0.04 | 0.08 |

Reaction conditions: glycerol: 3 g; 5% Pt/C: 0.2 g; NaOH/glycerol molar ratio: 1.1; $P_{N2}$: 14 bar; solvent: $H_2O$; initial liquid volume: 30 ml.

TABLE 6

Glycerol conversion under alkaline condition using platinum (Pt) catalyst in absence and presence of externally added hydrogen

|  | Nitrogen (14 bar) | | Hydrogen (41 bar) | |
|---|---|---|---|---|
|  | 433 K, 2 h | 433 K, 6 h | 433 K, 2 h | 433 K, 6 h |
| Glycerol conversion, % | 44.90 | 78.66 | 37.30 | 64.79 |
| Liquid phase product selectivity, % | | | | |
| Glyceraldehyde | 0.34 | 0.18 | 0.00 | 0.00 |
| Pyruvaldehyde | 0.67 | 0.37 | 0.00 | 0.00 |
| Ethylene glycol | 1.57 | 1.85 | 2.06 | 2.18 |
| 1,2-Propanediol | 20.85 | 36.54 | 53.77 | 57.37 |
| Lactic acid | 54.14 | 25.84 | 30.84 | 28.45 |
| Acetic acid | 0.00 | 1.23 | 0.00 | 0.00 |
| Methanol | 10.76 | 9.47 | 0.00 | 0.86 |
| Ethanol | 4.93 | 8.24 | 2.47 | 2.64 |
| 2-Propanol | 2.02 | 3.88 | 0.00 | 0.00 |
| Gas phase product selectivity, % | | | | |
| Methane | 0.16 | 1.02 | 0.17 | 1.49 |
| Ethane | 0.09 | 0.27 | 0.04 | 0.02 |
| Propane | 0.06 | 0.68 | 0.00 | 0.05 |
| Butane | 0.00 | 0.00 | 0.00 | 0.00 |
| Pentane | 0.04 | 0.08 | 0.20 | 0.09 |

Reaction conditions: glycerol: 3 g; 5% Pt/C: 0.2 g; NaOH/glycerol molar ratio: 1.1; solvent: $H_2O$; initial liquid volume: 30 ml.

EXAMPLE 2F

Ruthenium

The results with carbon-supported ruthenium catalyst (Ru/C) for glycerol conversion under alkaline condition (Table 7) indicate that the selectivity to lactic acid remained identical (30-40%) at 493 K and 433 K at various batch reaction times. However, reforming, water gas shift reaction (formation of $CO_2$) and methanation reactions are significantly lower at lower temperatures. Unlike Pt catalyst (Table 5), there is no change in product selectivity with batch time in the case of the Ru catalyst.

TABLE 7

Glycerol conversion under alkaline condition using ruthenium (Ru) catalyst

|  | 493 K, 6 h | 433 K, 2 h | 433 K, 6 h |
|---|---|---|---|
| Glycerol conversion, % | 97.66 | 51.83 | 83.86 |
| Liquid phase product selectivity, % | | | |
| Glyceraldehyde | 0.15 | 0.00 | 0.00 |
| Pyruvaldehyde | 0.30 | 0.88 | 0.53 |
| Ethylene glycol | 0.00 | 2.75 | 2.12 |
| 1,2-Propanediol | 4.79 | 36.28 | 35.85 |
| Lactic acid | 39.64 | 30.38 | 32.49 |
| Acetic acid | 1.60 | 1.77 | 5.30 |
| Methanol | 8.58 | 13.08 | 12.42 |
| Ethanol | 3.29 | 5.31 | 3.77 |
| 2-Propanol | 1.35 | 2.06 | 1.77 |
| Gas phase product selectivity, % | | | |
| Methane | 15.83 | 2.43 | 3.28 |
| Ethane | 5.68 | 0.79 | 0.58 |
| Propane | 2.31 | 0.64 | 0.39 |
| Butane | 0.00 | 0.02 | 0.00 |
| Pentane | 0.68 | 0.18 | 0.16 |

Reaction conditions: glycerol: 3 g; 5% Ru/C: 0.2 g; NaOH/glycerol molar ratio: 1.1; $P_{N2}$: 14 bar; solvent: $H_2O$; initial liquid volume: 30 ml.

EXAMPLE 2G

Palladium

Glycerol conversion under alkaline condition in presence of Pd/C catalyst at 493 K and 463 K, and different batch times were explored and the product profiles are presented in Table 8. Lactic acid selectivity remained low and more or less identical (40-44%) in all the runs.

TABLE 8

Glycerol conversion under alkaline condition using palladium (Pd) catalyst

|  | 493 K, 6 h | 463 K, 2 h | 463 K, 6 h |
|---|---|---|---|
| Glycerol conversion, % | 91.09 | 65.02 | 86.78 |
| Liquid phase product selectivity, % | | | |
| Glyceraldehyde | 0.32 | 0.00 | 0.17 |
| Pyruvaldehyde | 0.16 | 0.00 | 0.00 |
| Ethylene glycol | 1.39 | 2.35 | 2.01 |
| 1,2-Propanediol | 6.90 | 13.63 | 13.06 |
| Lactic acid | 40.10 | 43.00 | 40.69 |
| Acetic acid | 2.78 | 2.04 | 2.12 |
| Methanol | 6.20 | 9.95 | 8.93 |
| Ethanol | 5.88 | 9.24 | 8.93 |
| 2-Propanol | 2.41 | 3.99 | 4.19 |
| Gas phase product selectivity, % | | | |
| Methane | 3.71 | 0.22 | 0.46 |
| Ethane | 0.07 | 0.01 | 0.01 |
| Propane | 0.32 | 0.02 | 0.04 |
| Butane | 0.00 | 0.00 | 0.00 |
| Pentane | 0.12 | 0.06 | 0.25 |

Reaction conditions: glycerol: 3 g; 5% Pd/C: 0.2 g; NaOH/glycerol molar ratio: 1.1; $P_{N2}$: 14 bar; solvent: $H_2O$; initial liquid volume: 30 ml.

EXAMPLE 2H

Rhodium

The intrinsic activity of Rh/C catalyst for glycerol conversion in alkaline medium was found to be lower (Table 9) compared to other precious metal catalysts discussed above. The selectivity to lactic acid changed marginally with changing operating temperature and batch time.

TABLE 9

Glycerol conversion under alkaline condition using rhodium (Rh) catalyst

|  | 493 K, 6 h | 433 K, 2 h | 433 K, 6 h |
|---|---|---|---|
| Glycerol conversion, % | 86.97 | 33.03 | 57.09 |
| Liquid phase product selectivity, % | | | |
| Glyceraldehyde | 0.16 | 0.00 | 0.00 |
| Pyruvaldehyde | 0.33 | 0.46 | 0.23 |
| Ethylene glycol | 0.99 | 0.93 | 1.24 |
| 1,2-Propanediol | 10.87 | 27.31 | 31.23 |
| Lactic acid | 37.88 | 46.30 | 46.85 |
| Acetic acid | 2.75 | 0.00 | 0.00 |
| Methanol | 9.94 | 10.03 | 9.62 |
| Ethanol | 3.60 | 4.01 | 3.35 |
| 2-Propanol | 1.48 | 1.85 | 1.85 |
| Gas phase product selectivity, % | | | |
| Methane | 7.86 | 4.09 | 3.92 |
| Ethane | 1.42 | 0.26 | 0.23 |
| Propane | 1.18 | 0.34 | 0.31 |
| Butane | 0.00 | 0.01 | 0.00 |
| Pentane | 0.28 | 0.01 | 0.01 |

Reaction conditions: glycerol: 3 g; 5% Rh/C: 0.2 g; NaOH/glycerol molar ratio: 1.1; $P_{N2}$: 14 bar; solvent: $H_2O$; initial liquid volume: 30 ml.

EXAMPLE 3

Effect of NaOH/Glycerol Molar Ratio

As shown in above mentioned scheme, the base accelerates lactic acid formation by (i) favoring the transformation of pyruvaldehyde to lactic acid, and (ii) shifting the equilibrium toward lactic acid formation (by reducing the lactic acid concentration as a result of Na-lactate formation). As lactate formation reduces the effective base concentration in the reaction mixture, the effect of NaOH/glycerol molar ratio was studied. In this example, the reaction conditions were as follows: glycerol:3 g; Cu/SiO$_2$:0.4 g; $P_{N2}$:14 bar; 513 K; solvent:$H_2O$; initial liquid volume: 30 ml; batch reaction time: 6 hours.

FIG. 1 shows a gradual increase in conversion of glycerol with increase in NaOH/glycerol ratio; however, the lactic acid selectivity remained constant above NaOH/glycerol ratio of 1. At NaOH/glycerol ratio <1, the final reaction mixture was neutral (pH: 7) indicating that there was no base left to catalyze the pyruvaldehyde to lactic acid reaction or scavenge lactic acid to shift the equilibrium. Consequently, conversion of glycerol decreased. At higher NaOH/glycerol ratios, the base catalyzed reactions should be able to proceed farther thereby reducing the effective concentration of glyceraldehyde, which indirectly favors the dehydrogenation equilibrium for glycerol conversion to glyceraldehyde. This might be a reason for the improved conversion of glycerol at the NaOH/glycerol molar ratio of 1.5. These results are significant compared to the hydrothermal synthesis described in Ramírez-López et al., *Synthesis of lactic acid by alkaline hydrothermal conversion of glycerol at high glycerol concentration*, Ind. Eng. Chem. Res. 49(14) 6270-6278 (2010) in which not only higher NaOH/glycerol ratio and high temperature (greater than 543 K) are required but the lactic acid selectivity is also lower due to decomposition of pyruvaldehyde and lactic acid.

EXAMPLE 4

Effect of Temperature

In this example, the effect of temperature was investigated in a reaction mixture having a copper dehydrogenation catalyst. As shown below, glycerol conversion increased significantly with increase in temperature (493-513 K) while, the selectivity to lactic acid remained identical (Table 10).

TABLE 10

Effect of temperature on glycerol conversion to lactic acid in presence of Cu/SiO$_2$ catalyst and NaOH

| Temperature | Glycerol conversion, % | Lactic acid selectivity, % |
|---|---|---|
| 473 K | 35.5 | 81.6 |
| 493 K | 44.5 | 81.5 |
| 513 K | 75.2 | 79.7 |

Reaction conditions: glycerol: 3 g; NaOH/glycerol molar ratio: 1.1; Cu/SiO$_2$: 0.4 g; $P_{N2}$: 14 bar; solvent: $H_2O$; initial liquid volume: 30 ml; batch reaction time: 6 hours.

Several experiments were also carried out using Cu$_2$O catalyst with different NaOH/glycerol ratios at different temperatures. As shown in Table 11, the Cu$_2$O catalyst provides high yield of lactic acid even at 473 K, a temperature at which the Cu/SiO$_2$ catalyst displays much lower yield (see Table 10). When compared to the hydrothermal process, the Cu$_2$O catalyst provides similar yield of lactic acid (about 80%) but at lower temperatures (by about 80-100 K).

TABLE 11

Cu$_2$O catalyst for conversion of glycerol to lactic acid under different temperature and NaOH/glycerol molar ratio

| Temperature | NaOH/glycerol molar ratio | Glycerol conversion, % | Lactic acid selectivity, % |
|---|---|---|---|
| 473 K | 1.1 | 70.2 | 79.2 |
|  | 1.5 | 95.1 | 80.3 |
| 493 K | 1.1 | 88.2 | 76.2 |
|  | 1.5 | 94.8 | 77.6 |
| 513 K | 1.1 | 93.6 | 78.1 |

Reaction conditions: glycerol: 3 g; Cu$_2$O: 0.2 g; $P_{N2}$: 14 bar; solvent: $H_2O$; initial liquid volume: 30 ml; batch reaction time: 6 hours.

EXAMPLE 5

Reuse of Cu$_2$O Catalyst

Figure 2:
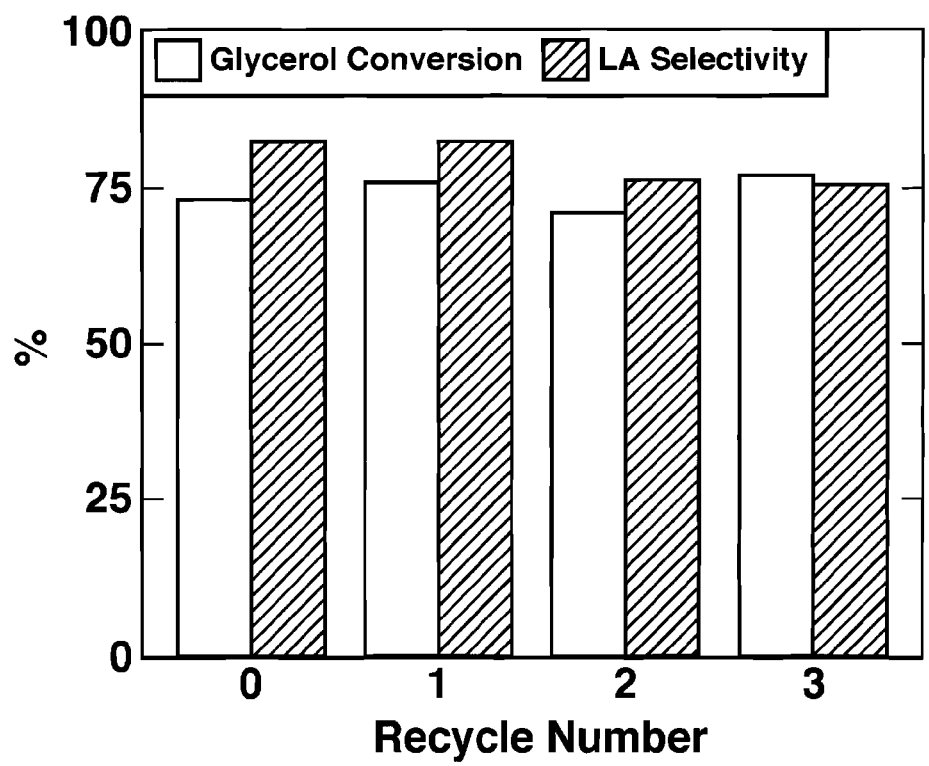
FIG. 2 shows the recycle study with Cu₂O catalyst. Reaction conditions: glycerol:3 g; Cu₂O:0.2 g; NaOH/glycerol molar ratio: 1.1; $P_{N2}$:14 bar; 473 K; solvent:H₂O; initial liquid volume: 30 ml; batch reaction time: 6 hours.

The reusability of the Cu$_2$O catalyst was tested by several recycle experiments at 473 K with 1.1 molar ratio of NaOH/glycerol. In this example, the reaction conditions were as follows: glycerol:3 g; Cu$_2$O:0.2 g; NaOH/glycerol molar ratio: 1.1; $P_{N2}$:14 bar; 473 K; solvent:$H_2O$; initial liquid volume: 30 ml; batch reaction time: 6 hours. As shown in FIG. 2, the glycerol conversion and lactic acid selectivity remained virtually identical during the recycle runs, indicating very good catalyst stability under reaction conditions.

In conclusion, copper catalysts, base metal catalysts, and precious metal catalysts have been tested for low temperature (e.g., about 473 K) conversion of glycerol to lactic acid. The experiments demonstrated that Cu based catalysts give high yields of lactic acid (about 80%). Compared to the hydrothermal process, this new catalytic route requires lower temperatures and glycerol/alkali ratios without the need for oxygen or hydrogen. The $Cu_2O$ catalyst in particular showed very good stability for prolonged use.

From the foregoing, it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A process for producing lactic acid from glycerol comprising forming a reaction mixture comprising glycerol, an alkaline component, water, and a dehydrogenation catalyst that is selected from the following:
   a copper catalyst selected from the group consisting of metallic copper (Cu), cuprous oxide ($Cu_2O$), cupric oxide (CuO), copper chromite ($Cu_2Cr_2O_5$);
   a Raney catalyst selected from the group consisting of a Raney nickel catalyst or a Raney cobalt catalyst; or
   an elemental catalyst selected from the group consisting of, elemental palladium, or elemental rhodium, wherein said elemental catalyst is supported on a support; and
   wherein the process is carried out without adding hydrogen or oxygen.

2. The process according to claim 1, wherein the process is carried out at a temperature maintained below about 250° C.

3. The process according to claim 1, wherein the process is carried out at a temperature maintained between about 180 to 240° C.

4. The process according to claim 1 wherein said dehydrogenation catalyst is supported on a support selected from the group consisting of carbon, silica, aluminas, titania, zirconia, and zeolites.

5. The process according to claim 1, wherein the alkaline component is an alkali, alkaline earth metal hydroxide, or solid base.

6. The process according to claim 1, wherein the alkaline component to glycerol molar ratio ranges between about 0.5 to 7.

7. The process according to claim 1 wherein the concentration of the glycerol ranges between about 10-50 wt % of the liquid in the reaction system.

8. The process according to claim 1, wherein the process is carried out at a pressure in the range from 10 to 50 bar.

9. The process according to claim 1, wherein the glycerol is produced from plant fats, animal fats, or biomass.

10. The process for producing lactic acid according to claim 1, wherein said process forms an aqueous solution comprising lactic acid and the alkaline component and further comprising the step of concentrating the lactic acid and the alkaline component using an electrodialysis process.

11. The process for producing lactic acid according to claim 1, wherein said process forms an aqueous solution comprising lactic acid and the alkaline component and further comprising the step of separating a solid lactate salt from said alkaline component present in the aqueous solution using a crystallization process.

12. The process according to claim 1 wherein the dehydrogenation catalyst is a copper catalyst, and where the process has a selectivity for lactic acid above about 60%.

13. The process according to claim 1 wherein the dehydrogenation catalyst comprises a Raney nickel catalyst or Raney copper catalyst and wherein said process has a glycerol conversion above about 80% and a selectivity for lactic acid above about 20%.

14. The process according to claim 1 wherein the dehydrogenation catalyst comprises a platinum dehydrogenation catalyst and wherein said process has a glycerol conversion above about 90% and a selectivity for lactic acid above about 35%.

15. The process according to claim 1 wherein the dehydrogenation catalyst comprises a ruthenium dehydrogenation catalyst, and wherein said process has a glycerol conversion above about 50% and a selectivity for lactic acid above about 30%.

16. The process according to claim 1 wherein the dehydrogenation catalyst comprises a ruthenium dehydrogenation catalyst, and wherein said process has a glycerol conversion above about 60% and a selectivity for lactic acid above about 40%.

17. The process according to claim 1 wherein the dehydrogenation catalyst comprises a rhodium dehydrogenation catalyst, and wherein said process has a glycerol conversion above about 50% and a selectivity for lactic acid above about 30%.

* * * * *